United States Patent
Newman et al.

[11] Patent Number: 5,954,713
[45] Date of Patent: Sep. 21, 1999

[54] ENDARTERECTOMY SURGICAL INSTRUMENTS AND PROCEDURE

[76] Inventors: Fredric A. Newman, 21 Wayside La., Scarsdale, N.Y. 10583; Martin J. Kaplitt, 271-32E Grand Central Pkwy, Floral Park, N.Y. 11005; William R. Knepshield, 11 Roselawn La., Malvern, Pa. 19355

[21] Appl. No.: 08/680,594

[22] Filed: Jul. 12, 1996

[51] Int. Cl.⁶ .................................................. A61B 17/36
[52] U.S. Cl. ............................................................ 606/15
[58] Field of Search ................... 606/2, 14, 15, 606/16, 17

[56] References Cited

U.S. PATENT DOCUMENTS

| | | | |
|---|---|---|---|
| 2,944,552 | 7/1960 | Cannon | 128/304 |
| 3,525,339 | 8/1970 | Halligan | 128/303 |
| 3,886,943 | 6/1975 | Skiff et al. | 128/305 |
| 3,903,892 | 9/1975 | Komiya | 128/303.15 |
| 4,968,314 | 11/1990 | Michaels | 606/15 |
| 5,254,115 | 10/1993 | Bhatta et al. | 606/16 |
| 5,267,994 | 12/1993 | Gentelia et al. | 606/15 |
| 5,285,795 | 2/1994 | Ryan et al. | 606/16 |
| 5,300,036 | 4/1994 | Mueller et al. . | |
| 5,309,896 | 5/1994 | Moll et al. . | |
| 5,342,358 | 8/1994 | Daikuzono | 606/16 |
| 5,361,752 | 11/1994 | Moll et al. . | |
| 5,397,335 | 3/1995 | Gresl et al. . | |
| 5,402,772 | 4/1995 | Moll et al. . | |
| 5,407,433 | 4/1995 | Loomas . | |
| 5,411,483 | 5/1995 | Loomas et al. . | |
| 5,425,357 | 6/1995 | Moll et al. . | |
| 5,437,660 | 8/1995 | Johnson et al. | 606/15 |
| 5,450,843 | 9/1995 | Moll et al. . | |
| 5,454,367 | 10/1995 | Moll et al. . | |
| 5,465,711 | 11/1995 | Moll et al. . | |
| 5,468,248 | 11/1995 | Chin et al. . | |
| 5,562,658 | 10/1996 | Long | 606/15 |
| 5,658,275 | 8/1997 | Saadat | 606/15 |

FOREIGN PATENT DOCUMENTS

| | | |
|---|---|---|
| 0 121 215 | 10/1984 | European Pat. Off. . |
| 26 12 315 | 9/1977 | Germany . |
| WO 95/11633 | 5/1995 | WIPO . |

OTHER PUBLICATIONS

Vaso View, Endoscopic Vessel Harvesting, Maximum Exposure Minimal Trauma, Guidant Origin Medsystems, 1997.
G. Ho, M.D. et al., The Mollring Cutter Remote Endarterectomy: Preliminary Experience with a New Endovascular Technique for Treatment of Occlusive Superficial Femoral Artery Disease, *J. Endovascular Surgery*, 1995; 2:278–287.
A. Bray, M.D., Superficial Femoral Endarterectomy with Intra-arterial PTFE Grafting, *J. Endovascular Surgery*, 1995; 2:297–301.
B. Hill, M.D. et al., Angioscopic Evaluation of an Endoluminal Aortic Graft: The First Clinical Experience, *J. Endovascular Surgery*, 1995; 2:248–254.
T. Fogarty, M.D., Oceans Apart: The Dichotomy in Superficial Femoral Endarterectomy, *J. Endovascular Surgery*, 1995; 2:288.

*Primary Examiner*—Michael Peffley
*Assistant Examiner*—Sonya Harris-Ogugua
*Attorney, Agent, or Firm*—Ostrolenk, Faber, Gerb & Soffen, LLP

[57] ABSTRACT

An endarterectomy surgical instrument and procedure for removing plaque from a selected length of an artery and surgical instruments for cutting plaque build-ups. The endarterectomy surgical instrument has means for developing an image of the surgical site so that probing of the artery can be observed without requiring opening the artery along the selected length over which the plaque is removed.

12 Claims, 4 Drawing Sheets

FIG. 4

ENDARTERECTOMY SURGICAL INSTRUMENTS AND PROCEDURE

TECHNICAL FIELD

The present invention relates, in general, to surgical instruments and procedures and, in particular, to the cleaning of arteries to remove plaque build-ups.

BACKGROUND OF THE INVENTION

It has been common practice to open the full selected length of an artery which is to be cleaned of plaque build-ups and tediously separate the inner layers (i.e. the "core") from the outer layers to remove the plaque build-ups along the length of the artery after which the full length of the opening is sutured closed using the outer layers for the closure. Because such incisions, for example, can extend along the entire length of the leg from the groin to the foot, such a procedure is a massive surgical invasion. As the length of the incision increases, the difficulty of the surgical procedure increases.

Another procedure, involving relatively small incisions at the ends of the artery section to be cleaned, also has been performed in the past for the removal of plaque build-ups. In this procedure, plaque build-ups are removed or loosened by forceps which are introduced at the two incisions to "core out" the artery. To remove residue plaque, a "stripper" (e.g. a catheter-type unit) is passed through the entire blocked artery from the upper incision to the lower incision and a certain, limited amount of residue plaque is pushed out through the lower incision. A swab is secured to the leading end of the catheter-type unit after it has emerged through the lower incision. Upon retraction of the catheter-type unit, the swab carries residue plaque toward and out from the upper incision. Thereafter, the two incisions are closed. Because this procedure is "blind" in that the artery section being cleaned is not open and exposed, it is inherently dangerous. Also, the second incision is necessary either for an exit of plaque or to gain access to the catheter-type unit for affixing the swab.

In another technique for the removal of plaque build-ups, known as gas endarterectomy, a jet of carbon dioxide gas is injected into the wall of an artery to create a "separation plane." A small opening is made in the artery and a special gas spatula, carefully designed not to injure the artery, is passed down the separation plane as carbon dioxide gas passes through the spatula further freeing up the entire length of the inner core. The inner core then is removed by transecting the distal end and pulling the entire core out of the proximal opening in the artery after which the two openings are closed. Because this procedure also is "blind" in that the artery section being cleaned is not open and exposed, it is inherently dangerous. Also, this procedure requires at least two surgical incisions to expose both ends of the artery section to be cleaned and two openings in the artery itself.

Gas endarterectomy also has been carried out by first surgically opening the body part, but not the artery which is to be cleaned, along the full selected length of the artery and then performing the gas endarterectomy by viewing the probing of the artery through the sufficiently transparent artery wall. Such a procedure also is a massive surgical invasion. As the length of the incision increases, the difficulty of the surgical procedure increases.

Because of the difficulties and hazards associated with the surgical procedures described above, bypass surgical procedures became popular. Instead of cleaning out a plaque build-up in an artery, the section of the artery having the plaque build-up is bypassed surgically. Such a bypass procedure also is a massive surgical invasion. As the length of the bypass increases, the difficulty of the surgical procedure increases.

At the present time, there is a trend for reducing the degree of invasion in surgical procedures. Consequently, more and more renewed interest is being expressed in gas endarterectomy which reduces surgical invasion and the period of time the patient must remain in the hospital.

SUMMARY OF THE INVENTION

The present invention is new surgical instruments and a new surgical procedure for performing gas endarterectomy through only one, relatively small incision.

An endarterectomy surgical instrument, constructed in accordance with the present invention, includes a spatula tip having at a first end thereof an optics opening and a plurality of fluid openings. This endarterectomy surgical instrument also has first flexible tubular means extending through the spatula tip from the optics opening in the spatula tip for conducting a light from a remote end of the first flexible tubular means through the optics opening to a surgical site and an image of the surgical site through the optics opening to the remote end of the first flexible tubular means. This endarterectomy surgical instrument also has second flexible tubular means extending through the spatula tip from the fluid openings in the spatula tip for conducting a fluid from a remote end of the second flexible tubular means through the fluid openings to the surgical site. This endarterectomy surgical instrument further has connector means adapted for connection to a light source, an image forming unit, and a fluid source and to which the remote end of the first flexible tubular means and the remote end of the second flexible tubular means are connected for conducting the light from the light source to the first flexible tubular means, the image of the surgical site from the first flexible tubular means to the image forming unit, and fluid from the fluid source to the second flexible tubular means.

An endarterectomy surgical procedure for removing a plaque build-up from a selected length of an artery, performed in accordance with the present invention, includes making only one incision at a first end of a selected length of an artery from which a plaque build-up is to be removed to expose the artery. This endarterectomy surgical procedure also includes inserting a spatula into the artery at the incision between the adventitia layer and the media layer of the artery and probing the selected length of the artery with the spatula while applying a fluid to increase the space between the adventitia layer and the media layer of the artery. This endarterectomy surgical procedure further includes continuously developing an image of the surgical site at the spatula as the artery is probed and viewing the image of the surgical site while probing the artery. Also included in this endarterectomy surgical procedure are terminating probing of the artery at a second end of the selected length of the artery and retracting the spatula and removing the spatula from the artery through the incision. Next, this endarterectomy surgical procedure includes removing the plaque build-up from the artery and treating the termination transition at the second end of the selected length of the artery. This endarterectomy surgical procedure is concluded by closing the incision.

If it is necessary to cut the plaque build-up so that it can be removed, a first surgical instrument, constructed in accordance with the present invention, includes an elongated flexible stem unit, a handle at a first end of the elongated flexible stem unit, and a cutting unit at a second end of the elongated flexible stem unit, opposite from the first end. The cutting unit has an inner cutting edge and a curved outer blunt edge.

A second surgical instrument, constructed in accordance with the present invention for cutting plaque build-ups, includes an elongated tubular support unit and a cutting wire unit extending through the elongated tubular support unit and freely movable within the elongated tubular support unit. The free ends of the cutting wire unit project from a first end of the elongated tubular support unit and a closed loop portion of the cutting wire unit projects from a second end of the elongated tubular support unit.

DETAILED DESCRIPTION OF THE INVENTION

Figure 1:
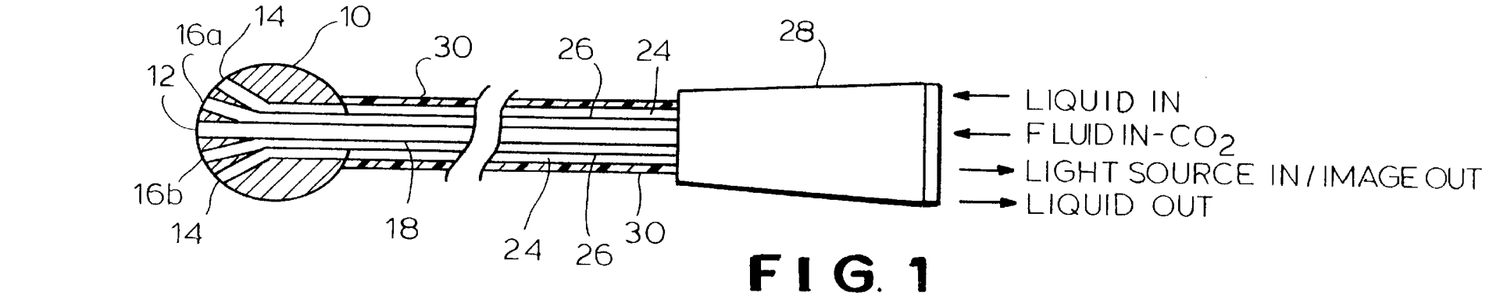
FIG. 1 is a top view, partially in cross-section, of an endarterectomy surgical instrument constructed in accordance with the present invention.
Figure 2:
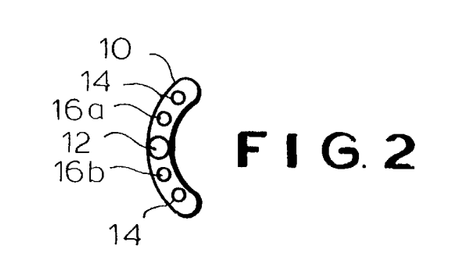
FIG. 2 is an end view of the spatula tip portion of the endarterectomy surgical instrument of FIG. 1.
Figure 3:
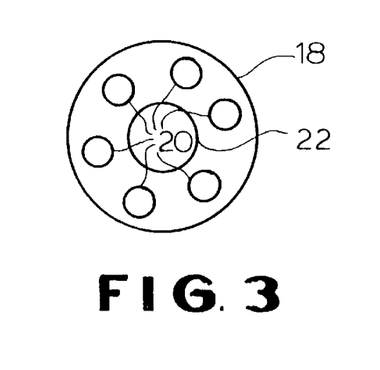
FIG. 3 is a sectional view of the optics portion of the endarterectomy surgical instrument of FIG. 1.

Referring to FIGS. 1, 2 and 3, an endarterectomy surgical instrument, constructed in accordance with the present invention, includes a spatula tip 10 having at a first end thereof an optics (i.e. light and image) opening 12 and a plurality of fluid openings 14. As will be explained below, optics opening 12 permits a light from a light source to be conducted to a surgical site and an image of the surgical site to be conducted to an image forming unit. In this way, the surgeon can observe the surgical procedure being conducted within the artery without the need to open the entire length of the artery which is being cleaned. As will also be explained below, fluid openings 14 permit the passage of a fluid, typically carbon dioxide, to the surgical site to increase the space (i.e. the "separation plane") between the adventitia layer and the media layer of the artery. In this way, spatula tip 10 can be advanced along the length of the artery which is being cleaned. Spatula tip 10 preferably has a curved body which approximates the shape of an artery and is sized for the particular artery being cleaned.

Preferably, spatula tip 10 also has at the first end thereof a plurality of liquid openings 16a and 16b to permit the passage of a liquid to and from the surgical site to carry away plaque debris and clean optics opening 12. The liquid is conducted to the surgical site through liquid opening 16a and is conducted away from the surgical site through liquid opening 16b. Typically, the liquid can be a saline solution.

An endarterectomy surgical instrument, constructed in accordance with the present invention, also includes first flexible tubular means 18 extending through spatula tip 10 from optics opening 12 in the spatula tip for conducting a light from a remote end of the first flexible tubular means through the optics opening to a surgical site and an image of the surgical site through the optics opening to the remote end of the first flexible tubular means. Such first flexible tubular means 18 can include first fiber optic means through which light is conducted to the surgical site and second fiber optic means through which an image of the surgical site is conducted. For the embodiment of the invention shown in FIG. 3, the first fiber optic means include a plurality of fiber optic cables 20 disposed in a circular array and the second fiber optic means include a single fiber optic cable 22 disposed at the center of the circular array of the plurality of fiber optic cables 20 of the first fiber optic means. As shown in FIGS. 1 and 2, optics opening 12 and fiber optic cables 20 and 22 preferably are within the curved body of spatula tip 10 rather than outside the inner and outer curved surfaces of the spatula tip to facilitate the design and minimize the size of the spatula tip.

An endarterectomy surgical instrument, constructed in accordance with the present invention, further includes second flexible tubular means 24 extending through 10 spatula tip from fluid openings 14 in the spatula tip for conducting a fluid from a remote end of the second flexible tubular means through the fluid openings to the surgical site.

Although first flexible tubular means 18 and second flexible tubular means 24 are shown as being spaced apart, they can be arranged in a coaxial manner.

When a liquid is to be delivered to the surgical site, an endarterectomy surgical instrument, constructed in accordance with present invention, further includes third flexible tubular means 26 extending through spatula tip 10 from liquid openings 16a and 16b in the spatula tip for conducting liquid from a remote end of the third flexible tubular means to the surgical site through a first of the liquid openings and for conducting liquid through a second of the liquid openings from the surgical site to the remote end of the third flexible tubular means.

An endarterectomy surgical instrument, constructed in accordance with present invention, also includes connector means 28 adapted for connection to a light source, an image forming unit, and a fluid source and to which the remote end of first flexible tubular means 18 and the remote end of second flexible tubular means 24 are connected. When liquid is to delivered to and drawn from the surgical site, connector means 28 are adapted for connection to a liquid source and a liquid discharge reservoir and the remote end of third flexible tubular means 26 are connected to the connector means. In this way, light from the light source is conducted to first flexible tubular means 18, an image of the surgical site is conducted from first flexible tubular means 18 to the image forming unit, fluid from the fluid source is conducted to second flexible tubular means 24, and liquid is to delivered from the liquid source to third flexible tubular means 26 and delivered from the third flexible tubular means to the liquid discharge reservoir.

Connector means 28 can include conventional luer lock connectors to which the fluid source and second flexible tubular means 24 are connected for the passage of fluid and to which the liquid source, liquid discharge reservoir and third flexible tubular means 26 are connected for the passage of saline solution. In contrast, the first fiber optic means through which light is conducted to the surgical site and the second fiber optic means through which the image of the surgical site is conducted to the image forming unit are continuous, uninterrupted fiber optic cables which pass through connector means 28 but are locked by the connector means against longitudinal and rotational sliding and sealed to prevent escape of carbon dioxide gas and saline solution.

Preferably, an endarterectomy surgical instrument, constructed in accordance with the present invention, includes a flexible sheathing 30 extending between spatula tip 10 and connector means 28 and through which first flexible tubular means 18, second flexible tubular means 24 and third flexible tubular means 26 extend. Flexible sheathing 30 can be a tubular piece, as shown in FIG. 1, through which separately formed first tubular means 18, second tubular means 24 and third flexible tubular means 26 extend or the sheathing and the tubular means can be formed as a single, flexible extruded piece with passages or channels through which the light, the image of the surgical site, the fluid and the saline solution are conducted.

The surgical instrument just described can be used in an endarterectomy surgical procedure for removing a plaque build-up from a selected length of an artery in accordance with the present invention. First, an incision is made and the artery is dissected at a first end of a selected length of the artery from which a plaque build-up is to be removed. Next, the outer wall of the artery is penetrated with a needle, typically 25 gauge, and carbon dioxide gas is introduced through the needle to start the separation of the adventitia layer and the media layer (i.e. the "separation plane"). The needle is removed and an incision is made into the artery wall.

Figure 4:
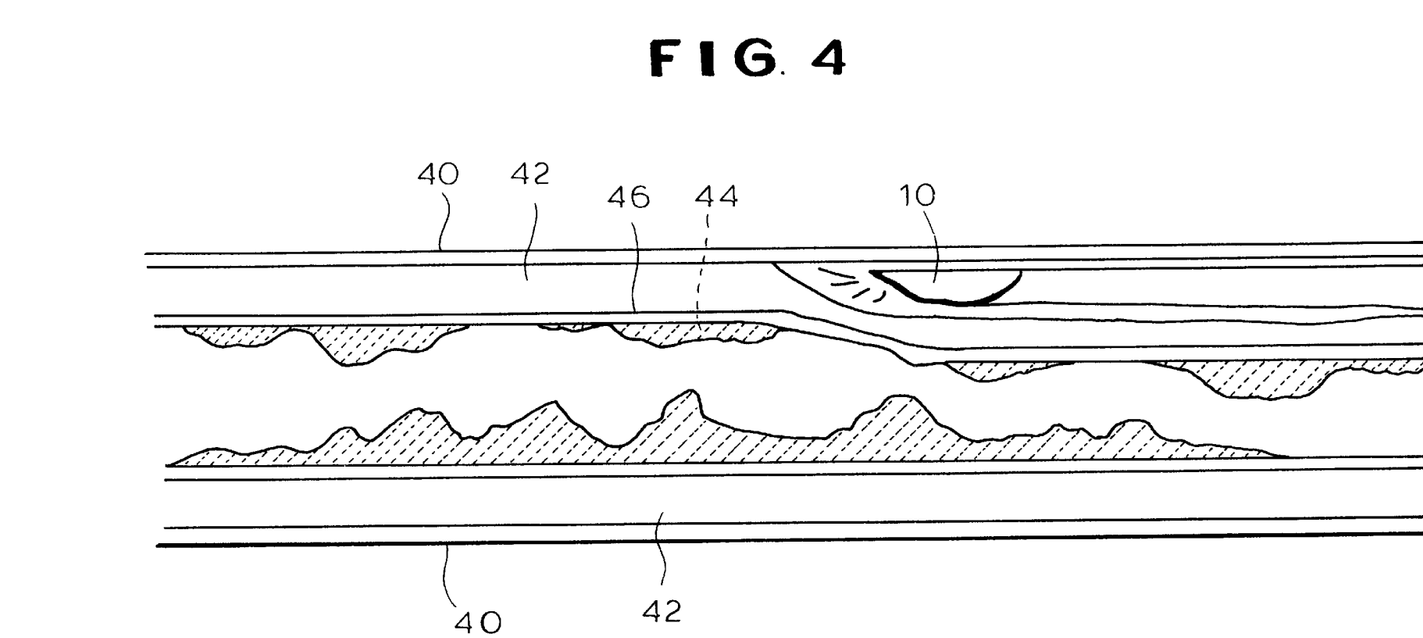
FIG. 4 is a sectional view of a human artery partially filled with plaque build-ups.

Referring to FIG. 4, the next step in the endarterectomy surgical procedure, performed in accordance with the present invention, is inserting a spatula 10 into the artery at the incision between the adventitia layer 40 and the media layer 42 of the artery. Next, the selected length of the artery is probed with the spatula while applying a fluid (e.g. carbon dioxide gas) under a controlled pressure through the spatula tip to increase the space between the adventitia layer 40 and the media layer 42 of the artery. The carbon dioxide gas also reduces the amount of blood at the surgical site. The carbon dioxide gas is either absorbed or flows out through the incision in the artery wall. Saline solution, under a controlled pressure, can be delivered to the surgical site to flush away pieces of plaque which have broken away from the plaque build-up 44 and to clean the optics opening in the spatula tip. It is important to control the pressures of the carbon dioxide gas and saline solution to eliminate the potential for creating damage to the artery when there is a total blockage of the artery by the plaque build-up.

As the artery is being probed, an image of the surgical site at the spatula is continuously developed, so that the surgeon performing the procedure can view the image of the surgical site while probing the artery. Side branches of the artery are isolated as the artery is probed. Probing of the artery is terminated at a second end of the selected length of the artery and the spatula is retracted and removed from the artery through the incision.

Next, the plaque build-up 44, along with the intima layer 46 and the media layer 42 of the artery (i.e. the "core"), are removed from the artery. The core can be removed by pulling the plaque build-up out through the incision with forceps if the plaque has been broken or weakened at the second end of the selected length of the artery. This can be determined by viewing the image of the surgical site as the spatula is moved along the artery.

If necessary, after the spatula has been retracted and removed from the artery a surgical instrument, such as the ones illustrated in FIGS. 7A, 7B, 7C and 8, can be inserted into the artery through the incision and advanced to the second end of the selected length of the artery at which the plaque build-up is cut. When the surgical cutting instrument is retracted and removed from the artery, the plaque build-up is pulled out through the incision by the surgical cutting instrument or with forceps.

After the plaque build-up has been removed, the termination transition at the second end of the selected length of the artery is treated and the incision is closed. If the spatula is arranged with liquid openings, liquid can be delivered to the surgical site and drawn away from the surgical site while the artery is being probed. It is important to remove plaque debris from the artery before the incision is closed.

Figure 5:
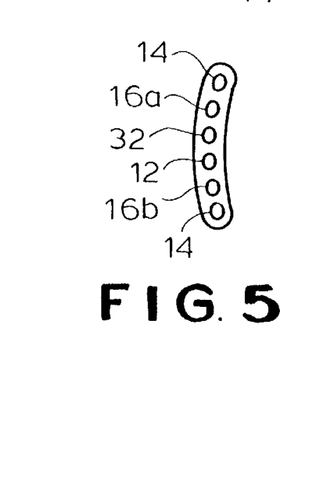
FIG. 5 is an end view of a second embodiment of the spatula tip portion of the endarterectomy surgical instrument of FIG. 1.

It is important to prepare the termination transition or there can be further stripping of plaque by blood flow. There is also the potential for clotting and debris at the termination if the transition is abrupt. The termination transition can be prepared by a laser instrument which can be included in an endarterectomy surgical instrument constructed in accordance with the present invention. As shown in FIG. 5, spatula tip 10 can have a laser opening 32 through which a laser beam can be emitted to prepare the termination transition.

Figure 6:
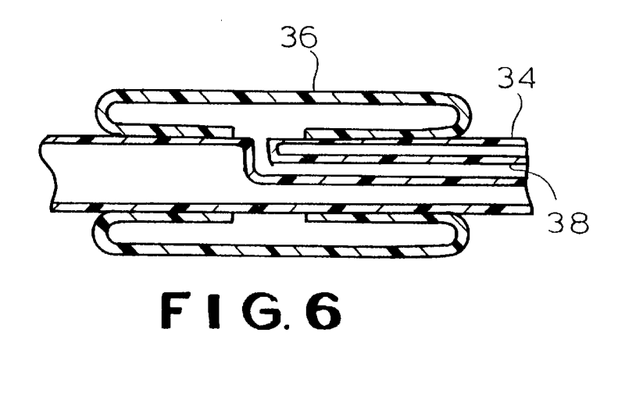
FIG. 6 is a sectional view of a portion of a third embodiment an endarterectomy surgical instrument constructed in accordance with the present invention.

As shown in FIG. 6, an endarterectomy surgical instrument, constructed in accordance with the present invention, can be arranged with a balloon and used in a surgical procedure in the same way that a balloon catheter is used. The flexible sheathing 34 has a balloon 36 bonded to the outside surface of the sheathing. With balloon 36 deflated, it lies flat against the outside surface of flexible sheathing 34. When a fluid, under controlled pressure, is introduced into balloon 36 through air passage 38, the balloon inflates as shown in FIG. 6.

Figure 7A:
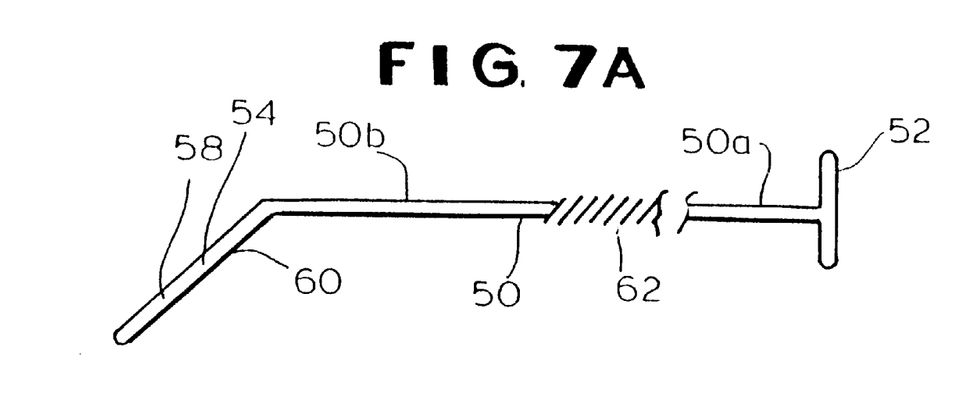
FIGS. 7A and 7B are top and side views, respectively, of a first embodiment of a surgical instrument, constructed in accordance with the present invention, for cutting plaque build-ups.
Figure 7B:
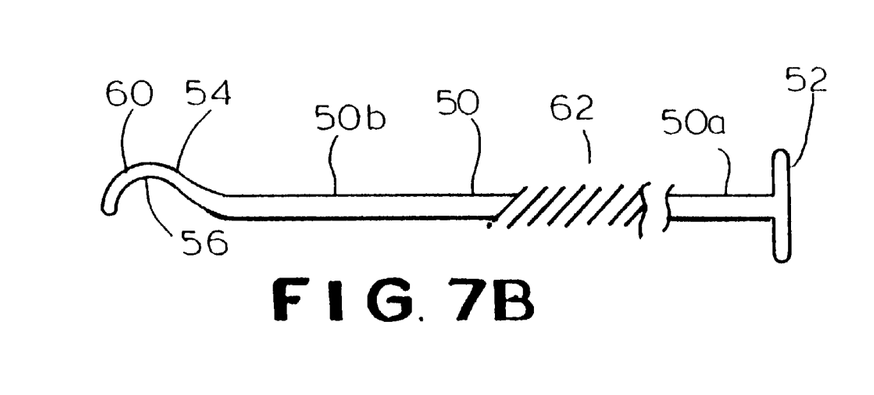

Referring to FIGS. 7A and 7B, a first embodiment of a surgical instrument for cutting plaque build-ups, constructed in accordance with the present invention, includes an elongated flexible stem unit 50, a handle 52 at a first end of the elongated flexible stem unit, and a cutting unit 54 at a second end of the elongated flexible stem unit, opposite from the first end. Cutting unit 54 has an inner cutting edge 56 and a curved outer blunt edge 58. A wall 60, extending between the inner cutting edge 56 and the curved outer blunt edge 58, has sufficient width to carry material which has been cut as handle 52 is pulled or turned. Although cutting edge 56 is shown as being curved, it can take other forms, such as a straight edge.

Preferably, cutting unit 54 of the surgical instrument of FIGS. 7A and 7B lies in a plane which is disposed at an obtuse angle relative to elongated stem unit 50. With such an arrangement, after the surgical instrument is introduced through the incision, cutting unit 54 is moved easily along the surface of the core which will be removed from the artery to the point at which the cutting unit is to cut the plaque build-up. As side branches of plaque build-ups are encountered, the surgical instrument can be rotated to bypass such side branches. For a particular surgical instrument for cutting plaque build-ups, the flexibility of stem unit 50, the angle between cutting unit 54 and the stem unit and the shape, radius and length of cutting edge 56 are dependent upon the size and condition of the artery. The objective of the design of any such surgical instrument is to assure that as the surgical instrument is turned to cut through the plaque build-up, the surgical instrument does not cut through the artery wall. The desired effect is to have cutting unit 54 encircle the plaque build-up as it cuts through the plaque build-up. When the cutting is completed, the cutting unit 54 can remain engaged with the core material which has been cut to an extent sufficient to remove the core material through the incision as the surgical instrument is retracted and removed through the incision. Wall 60, extending between inner cutting edge 56 and outer blunt edge 58, also is effective in removing the cut core material through the incision.

The desired flexibility in stem unit 50 of the surgical instrument illustrated by FIGS. 7A and 7B is provided by a spring 62 between a first end of a first rigid member 50a and a first end of a second rigid member 50b. Handle 52 is attached to a second end of first rigid member 50a of the elongated flexible stem unit and cutting unit 54 is attached to a second end of second rigid member 50b of the elongated flexible stem unit. Spring 62 and the cant of cutting unit 54 provide a center of rotation of the cutting unit which prevents cutting the artery wall as handle 52 is turned to cut a plaque build-up. Spring 62 is designed to be sufficiently flexible to achieve this result, yet sufficiently rigid to cut a plaque build-up and permit carrying material which has been cut as handle 52 is pulled or retracted from the incision.

Figure 7C:
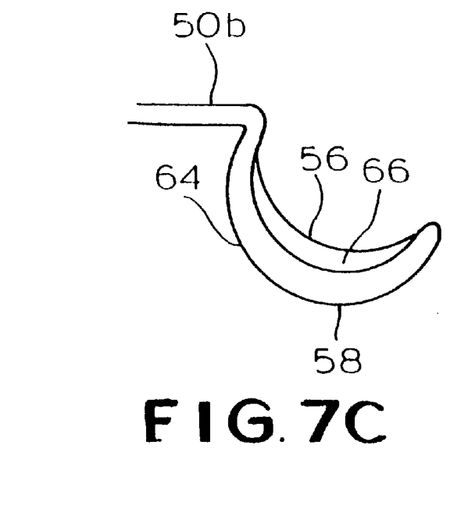
FIG. 7C shows an alternative form of the cutting unit portion of the surgical instrument of FIGS. 7A and 7B.

As shown in FIG. 7C, cutting unit 54 can be formed with a housing 64 which is attached to a second end of second rigid member 50b of the elongated stem unit and has a curved outer blunt edge 58. A cutting blade 66 is positioned within housing 64. With this form of cutting unit, there is a wall which extends between inner cutting edge 56 of cutting blade 66 and outer blunt edge 58 of housing 64 and has sufficient width to carry material which has been cut as handle 52 is pulled.

It should be noted that a surgical instrument for cutting plaque build-ups, such as the one illustrated in FIGS. 7A, 7B and 7C, can be arranged with optics and irrigation as is the endarterectomy surgical instrument described above.

Figure 8:
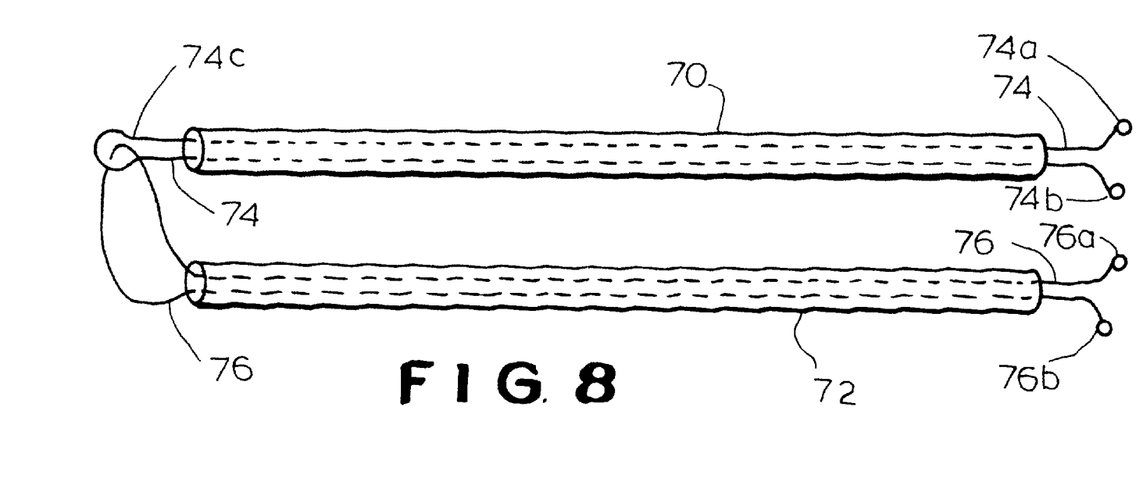
FIG. 8 is top view of a second embodiment of a surgical instrument, constructed in accordance with the present invention, for cutting plaque build-ups.
Figure 9:
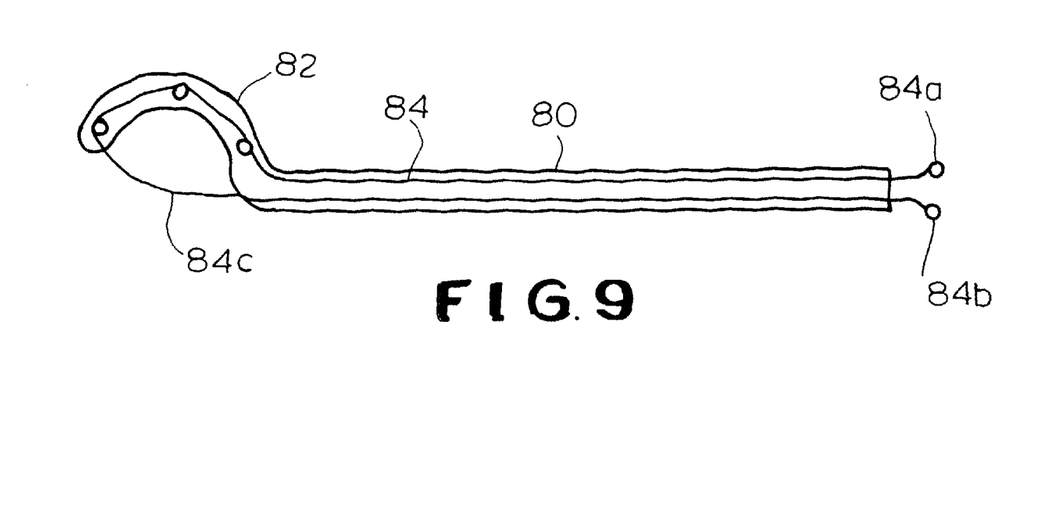
FIG. 9 is an open, side view of a third embodiment of a 1s surgical instrument, constructed in accordance with the present invention, for cutting plaque build-ups.

FIGS. 8 and 9 show second and third embodiments of a surgical instrument for cutting plaque build-ups constructed in accordance with the present invention. Each of these surgical instruments includes an elongated tubular support unit and a cutting wire unit extending through the elongated tubular support unit and freely movable within the elongated tubular support unit. The free ends of the cutting wire unit project from one end of the elongated tubular support unit and a closed loop portion of cutting wire unit projects from a second end of the elongated tubular support unit.

Referring to FIG. 8, the elongated tubular support unit includes a first elongated tube 70 and a second elongated tube 72. The cutting wire unit includes first and second lengths of wire 74 and 76 which extend through first elongated tube 70 and second elongated tube 72, respectively. First and second free ends 74a and 74b of the first length of wire project from one end of the first elongated tube and a middle portion 74c of the first length of wire projects from the opposite end of the first elongated tube. First and second free ends 76a and 76b of the second length of wire project from one end of the second elongated tube and a middle portion 76c of the second length of wire projects from the opposite second end of the second elongated tube and is looped through middle portion 74c of the first length of wire 74.

The surgical instrument of FIG. 8 is used in the following manner. The surgical instrument is introduced through the incision and is moved along the artery with middle portion 76c of wire 76 positioned outside the core material which is to be cut to the point at which the plaque build-up is to be cut. By pulling on the free ends 74a and 74b of wire 74 and the free 76a and 76b of wire 76, the slack in middle portion 76c of wire 76 is taken up and the core material is cut. The core material can be removed either by retraction of the surgical instrument or with forceps if middle portion 76c of wire 76 moves through the core material without pulling the core material through the incision.

Referring to FIG. 9, the elongated tubular support unit includes an elongated tube 80 and a housing 82 attached to the elongated tube at a first end thereof. The cutting wire unit includes a length of wire 84 which extends through elongated tube 80 and housing 82 with first and second free ends 84a and 84b of the length of wire projecting from a second end of the elongated tube opposite from the first end of elongated tube. The middle portion 84c of the length of wire projects from the first end of elongated tube 80 and is looped from the elongated tube through housing 82 into the elongated tube.

The surgical instrument of FIG. 9 is used in much the same manner as the surgical instrument of FIG. 8. The surgical instrument is introduced through the incision and is moved along the artery with middle portion 84c of wire 84 positioned outside the core material which is to be cut to the point at which the plaque build-up is to be cut. By pulling on the free ends 84a and 84b of wire 84, the slack in middle portion 84c of the wire is taken up and the core material is cut. The core material can be removed either by retraction of the surgical instrument or with forceps. Housing 82 functions in much the same way as the wall in the surgical instrument of FIGS. 7A, 7B and 7C in pulling the cut core material as the surgical instrument is retracted and withdrawn through the incision.

While in the foregoing there have been described preferred embodiments of the present invention, it should be understood by those skilled in the art that various modifications and changes can be made without departing from the true spirit and scope of the present invention.

What is claimed:

1. An endarterectomy surgical instrument comprising:
   (A) a spatula tip having at a first end thereof:
      (a) an optics opening, and
      (b) a plurality of fluid openings;
   (B) first flexible tubular means extending through said spatula tip from said optics opening to a remote ends, said first flexible tubular means including a plurality of fiber optic cables disposed in a substantially circular array to conduct light from a light source, and at least one fiber optic cable disposed within said circular array to conduct an image of the surgical site to an image forming unit
   (C) second flexible tubular means extending through said spatula tip from said fluid openings in said spatula tip to said remote end
   (D) connector means connectable to:
      (a) the light source;
      (b) the image forming unit, and
      (c) a fluid source and to which:
         (a) said remote end of said first flexible tubular means, and (b) said remote end of said second flexible tubular means are connected for conducting:
  (i) the light from the light source to said first flexible tubular means,
  (ii) the image of the surgical site from said first flexible tubular means to the image forming unit, and
  (iii) fluid from the fluid source to said second flexible tubular means; and
(E) a flexible sheathing extending between said spatula tip and said connector means and through which said first flexible tubular means and said second flexible tubular means extend.

2. An endarterectomy surgical instrument according to claim 1 wherein said spatula tip has a curved body and said optics opening, said plurality of fiber optic cables and said at least one fiber optic cable are within said curved body of said spatula tip.

3. An endarterectomy surgical instrument according to claim 1 wherein:
  (a) said spatula tip also has at said first end thereof a plurality of liquid openings, and
  (b) said connector means also are adapted for connection to a liquid source and a liquid discharge reservoir; and further including:
  (c) third flexible tubular means extending through said spatula tip from said liquid openings in said spatula tip for conducting liquid from a remote end of said third flexible tubular means connected to said connector means to the surgical site through a first of said liquid openings and for conducting liquid through a second of said liquid openings from the surgical site to said remote end of said third flexible tubular means.

4. An endarterectomy surgical instrument according to claim 3 wherein said third flexible tubular means extend through said flexible sheathing.

5. An endarterectomy surgical instrument according to claim 1 wherein said spatula tip also has at said first end thereof a laser opening through which a laser beam is emitted.

6. An endarterectomy surgical instrument according to claim 1 further including:

(a) a balloon bonded to said sheathing, and
(b) a fluid passage through which a fluid, under controlled pressure, is introduced into said balloon to inflate said balloon.

7. An endarterectomy surgical instrument comprising:
(A) an elongated body having a spatula tip disposed at a first end thereof for use at a surgical site, said spatula tip including:
  (1) an optics opening, and
  (2) at least one first fluid opening adapted to be used in combination with a fluid apparatus to deliver fluid to the surgical site; and
(B) a fiber optics assembly coupled to said optics opening, said fiber optics assembly including
  (1) a plurality of fiber optic cables arranged in a substantially circular array to conduct light from a light source to the surgical site through said optics opening; and
  (2) at least one fiber optic cable disposed within said circular array to conduct an image of the surgical site to an image forming unit through said optics opening.

8. The endarterectomy surgical instrument of claim 7, wherein said fluid opening is adapted to receive a gas and the fluid apparatus is an apparatus for delivering the gas to said opening.

9. The endarterectomy surgical instrument of claim 8, wherein the gas is $CO_2$.

10. The endarterectomy surgical instrument of claim 7, wherein said spatula includes at least one second fluid opening adapted to be used in combination with a liquid apparatus to receive a liquid and deliver the liquid to the surgical site.

11. The endarterectomy surgical instrument of claim 10, wherein the spatula includes at least one third fluid opening adapted to be used in combination with a liquid apparatus to receive a liquid and carry the liquid from the surgical site.

12. The endarterectomy surgical instrument of claim 11, wherein the fluid is saline.

* * * * *

UNITED STATES PATENT AND TRADEMARK OFFICE
CERTIFICATE OF CORRECTION

PATENT NO.   : 5,954,713
DATED        : September 21, 1999
INVENTOR(S)  : Fredric A. Newman et al.

It is certified that error appears in the above-identified patent and that said Letters Patent is hereby corrected as shown below:

Column 4,
Line 33 - line 34, "10 spatula tip" should read -- spatula tip 10 --.
Line 64, delete "to" (second occurrence).

Column 8,
Line 58, "unit" should read -- unit; --.
Line 61, "end" should read -- end; --.

Column 9,
Lines 15, 20, 39 and 43, "claim 1" should read -- claim 1, --.
Line 36, "claim 3" should read -- claim 3, --.

Signed and Sealed this

Eighth Day of October, 2002

Attest:

JAMES E. ROGAN
Attesting Officer        Director of the United States Patent and Trademark Office

UNITED STATES PATENT AND TRADEMARK OFFICE
CERTIFICATE OF CORRECTION

PATENT NO. : 5,954,713  
DATED : September 21, 1999  
INVENTOR(S) : Fredric H. Newman et al.

Page 1 of 1

It is certified that error appears in the above-identified patent and that said Letters Patent is hereby corrected as shown below:

<u>Title page,</u>  
Item [76], Inventors, should read -- Fredric Newman, Darien, CT; Martin J. Kapliti, Floral, NY --

Signed and Sealed this

Seventh Day of October, 2003

JAMES E. ROGAN  
*Director of the United States Patent and Trademark Office*